US009841364B2

(12) United States Patent
Chen et al.

(10) Patent No.: US 9,841,364 B2
(45) Date of Patent: Dec. 12, 2017

(54) DEVICE FOR TESTING MIXED-MODE FATIGUE CRACK GROWTH RATE

(71) Applicant: Hefei General Machinery Research Institute, Hefei (CN)

(72) Inventors: Xuedong Chen, Hefei (CN); Defu Nie, Hefei (CN); Zhichao Fan, Hefei (CN); Qiaoguo Wu, Hefei (CN)

(73) Assignee: Hefei General Machinery Research Institute, Anhui (CN)

( * ) Notice: Subject to any disclaimer, the term of this patent is extended or adjusted under 35 U.S.C. 154(b) by 108 days.

(21) Appl. No.: 15/036,031

(22) PCT Filed: Jun. 4, 2014

(86) PCT No.: PCT/CN2014/079122
§ 371 (c)(1),
(2) Date: May 11, 2016

(87) PCT Pub. No.: WO2014/194816
PCT Pub. Date: Dec. 11, 2014

(65) Prior Publication Data
US 2016/0349161 A1   Dec. 1, 2016

(30) Foreign Application Priority Data
Jun. 7, 2013 (CN) .......................... 2013 1 0227160

(51) Int. Cl.
*G01N 3/00* (2006.01)
*G01N 3/34* (2006.01)
*G01N 3/32* (2006.01)

(52) U.S. Cl.
CPC ................. *G01N 3/34* (2013.01); *G01N 3/32* (2013.01); *G01N 2203/0064* (2013.01); *G01N 2203/0066* (2013.01); *G01N 2203/0073* (2013.01)

(58) Field of Classification Search
CPC .... G01N 3/34; G01N 3/32; G01N 2203/0064; G01N 2203/0066; G01N 2203/0073
(Continued)

(56) References Cited

U.S. PATENT DOCUMENTS 4,198,870 A   4/1980   Barker
4,574,642 A * 3/1986   Fleischman .............. G01N 3/32
                                                                73/799
(Continued)

FOREIGN PATENT DOCUMENTS

CN   2639875 Y   9/2004
CN   1924546 A   3/2007
(Continued)

OTHER PUBLICATIONS

International search report from an international application No. PCT/CN2014/079122 dated Aug. 22, 2014.
(Continued)

*Primary Examiner* — Max Noori
(74) *Attorney, Agent, or Firm* — Calfee, Halter & Griswold LLP (57) ABSTRACT

A device for testing mixed-mode fatigue crack growth rate includes a plate-like specimen, and a first fixture mechanism for exerting stretch, shear and torsion actions on the specimen via a second fixture mechanism. The second fixture mechanism is used for clamping the specimen and enabling the specimen to generate a mixed-mode fatigue crack in cooperation with the first fixture mechanism. The device further comprises a fatigue crack measurement instrument for measuring and recording the length of mixed-mode fatigue crack generated on the specimen.

8 Claims, 5 Drawing Sheets

(58) Field of Classification Search
USPC .......................................... 73/784, 856, 794
See application file for complete search history.

(56) References Cited

U.S. PATENT DOCUMENTS

| | | | | |
|---|---|---|---|---|
| 6,860,156 B1* | 3/2005 | Cavallaro | ................ | G01N 3/08 73/813 |
| 7,204,160 B1* | 4/2007 | Sadegh | .................... | G01N 3/10 73/862.041 |
| 8,082,802 B1* | 12/2011 | Sadegh | .................... | G01N 3/08 73/760 |
| 2009/0133381 A1* | 5/2009 | Holmes | ................ | G01M 15/14 60/204 |

FOREIGN PATENT DOCUMENTS

| CN | 1987407 A | 6/2007 |
|---|---|---|
| CN | 102095680 A | 6/2011 |
| CN | 102156069 A | 8/2011 |
| CN | 102262016 A | 11/2011 |
| CN | 102564870 A | 7/2012 |
| CN | 202649026 U | 1/2013 |
| CN | 203178137 U | 9/2013 |
| JP | H194239 A | 4/1989 |
| KR | 101200250 B1 | 11/2012 |

OTHER PUBLICATIONS

International preliminary report and written opinion from an international application No. PCT/CN2014/079122 dated Dec. 8, 2015.
Changhai Tian, et al., "Mixed Mode Crack Propagation Test", Journal of University of Science and Technology Beijing, vol. 23, Sep. 2001, pp. 128-130.
J. Qian, et al., "Mixed Mode Fatigue Crack Growth: A Literature Survay", Engineering Fracture Mechanics, vol. 55, No. 6, 1996, pp. 969-990.
"The Fatigue Crack Direction and Threshold Behavior of Mild Steel Under Mixed Mode I and III Loading", International Journal of Fatigue, 7(1):21-30, Jan. 1985, accessed on https://www.researchgate.net/publication/248524496_The_Fatigue_Crack_Direction_and_Threshold_Behavior_of_Mild_Steel_Under_Mixed_Mode_I_and_III_Loading.
Weiping Yang, et al., "Study of Mixed Crack Growth in Friction Stir Welded Plates with Offset Hole", Advances in Aeronautical Science and Engineering, vol. 1, No. 2, May 2010, pp. 116-119.
Office Action including search report from Chinese Application No. 201310227160.5 dated Mar. 3, 2016.

* cited by examiner

DEVICE FOR TESTING MIXED-MODE FATIGUE CRACK GROWTH RATE

CROSS-REFERENCE TO RELATED APPLICATIONS

This application is a National Phase Application of International Application PCT/CN2014/079122, with an international filing date of Jun. 4, 2014, which is based on and claims priority to Chinese Patent Application No. 201310227160.5, filed on Jun. 7, 2013, the entire contents of which are incorporated herein by reference.

FIELD OF THE INVENTION

The present invention pertains to the field of material testing technology and relates to a device for testing mixed-mode fatigue crack growth rate.

BACKGROUND OF THE INVENTION

Fatigue failure is one of the major failure modes of mechanical parts and engineering components. It is mostly in a form of brittle failure and liable to causing heavy economic and property loss. Therefore, for a long time, the problem of fatigue failure has aroused wide concerns. Through enormous experimental research and practical engineering application, some description methods of fatigue failure have been formed based on different concepts. Among them, the fatigue crack growth rate description method formed based on the concept of damage tolerance has achieved a good effect in the fatigue life evaluation of cracking members. Fatigue crack growth rate is not only an important parameter representing resistance of a material to fatigue crack growth but also an important extension of the design concept of fatigue strength and total life based on elastic-plastic mechanics. With the constant development and perfection of fracture mechanics, this method is gaining more extensive application in fatigue design and analysis. For mechanical parts and engineering components, due to complex structure and working conditions, fatigue failure is mostly in a mixed mode, so the research on failure resulting from mixed-mode fatigue crack growth has very important theoretical significance and engineering value.

In view of fatigue crack and stress, fatigue cracks may be classified into mode I (the crack endures the action of vertical normal stress), mode II (the crack endures the action of in-plane shear stress) and mode III (the crack endures the action of out-of-plane shear stress). At present, many experiment researches have been done on fatigue crack growth rate, but they mostly use standard fixtures and specimens to test the growth rate under the action of mode-I fatigue load, while little is researched on mode II, mode III and mixed-mode fatigue crack growth rates and little experimental data is available. Today, commercial fatigue testing machines are dominated by axial tension-compression testing machines. Even if an axial tension-compression+torsion testing machine is adopted, standard fixtures and specimens can be used in mode I, mode III, and mode I-III mixed-mode fatigue crack growth tests only. Knowing the growth rates of cracks under the actions of various types of fatigue loads will help realize precise prediction on fatigue life of mechanical parts and engineering components in a complex stress field.

SUMMARY OF THE INVENTION

The object of the present invention is to provide a device for testing mixed-mode fatigue crack growth rate, which can effectively measure the growth rates of various kinds of mixed-mode fatigue cracks, realize crack growth tests under the action of mixed-mode fatigue load and research the fatigue crack growth law of a material under the action of a complex alternate stress field, thereby providing a reference and basis for precise prediction of fatigue life of critical mechanical parts and engineering components under complex working conditions.

In order to realize the foregoing object, the present invention adopts the following technical scheme: a device for testing mixed-mode fatigue crack growth rate, comprising a plate-like specimen and the following components:

a first fixture mechanism, for exerting stretch, shear and torsion actions on the specimen via a second fixture mechanism;

a second fixture mechanism, for clamping the specimen and enabling the specimen to generate a mixed-mode fatigue crack in cooperation with the first fixture mechanism;

a fatigue crack measurement instrument, for measuring and recording the length of a mixed-mode fatigue crack generated on the specimen.

Meanwhile, the present invention may be further realized through the following measures:

Preferably, the first fixture mechanism comprising two first fixtures, one end of each first fixture is designed as a cylindrical long rod, and the other end is designed as a U-shaped clamping portion making for connection to the fixture in a second fixture mechanism; the long rod and U-shaped clamping portion are integrally formed.

Preferably, the second fixture mechanism comprises a first flange type fixture and a second flange type fixture both comprising integrally formed flange plate and flange neck. The flange plates and the flange necks are all sectorial. A number of loading holes penetrating the plate body are evenly distributed along the circumference of each flange plate and on the arc edge of the flange plate sticking out from the corresponding flange neck.

A clamp face making for installation of the specimen is disposed at the circle center of the sectorial flange neck and perpendicular to the plane of the flange plate. The flange neck of the first flange type fixture and the flange neck of the second flange type fixture clamp and fix the specimen from the two side faces of the specimen respectively and insulating connecting components pass through the specimen, stretch into the flange neck and fasten the specimen to the clamp face; insulating spacers are disposed between the clamp face and the side face of the specimen; the flange plate of the first flange type fixture and the flange plate of the second flange type fixture in a clamping state are coplanar and have a same radius and circle center.

The U-shaped clamping portion of the first fixture is connected to a loading hole on a flange plate via a connecting component in a fixed manner. The U-shaped clamping portions on the two first fixtures are connected to the flange plate of the first flange type fixture and the flange plate of the second flange type fixture respectively. The center of the loading hole on the flange plate of the first flange type fixture connected to a U-shaped clamping portion and the center of the loading hole on the flange plate of the second flange type fixture jointly constitute a loading line. The loading line passes through the circle center of the flange plates.

The loading line is coplanar with the plane of the prefabricated fatigue crack generated on the specimen when the two first fixtures exert a stretch action on the specimen.

Preferably, the plate-like specimen is rectangular. A machining notch stretching from the edge of the specimen to the inside of the specimen along the width direction of the specimen is disposed on the specimen. The machining notch is disposed in the middle of a long side of the specimen. The closed end of the machining notch inside the specimen is in a peak shape. The crest line of the peak-shaped closed end of the machining notch is coplanar with the plane of the prefabricated fatigue crack. Mounting holes for the passage of the insulating connecting components are disposed on the two sides of the machining notch. The connecting line of the centers of the mounting holes is perpendicular to the plane of the prefabricated fatigue crack.

Further, the concentric angle corresponding to the flange plate of the first flange type fixture and the concentric angle corresponding to the flange plate of the second flange type fixture are both 90°.

Further, 5~9 loading holes are evenly distributed on each flange plate, and the two flange plates have a same number of loading holes.

Preferably, the connecting components are fastening bolts. The screws of the bolts pass through the U-shaped clamping portions and the loading holes and connect the first fixtures and flange plates. The ends of the screws of the bolts sticking out from the U-shaped clamping portions are fastened with nuts.

Preferably, the insulating connecting components are insulating bolts. Threaded holes corresponding to the insulating bolts are disposed on the clamp faces of the flange necks.

Preferably, the fatigue crack measurement instrument is a DC potential fatigue crack measurement instrument. The two voltage probes of the DC potential fatigue crack measurement instrument are connected to the two sides of the open end of the machining notch respectively. The two current probes of the DC potential fatigue crack measurement instrument are respectively connected to the intersections between the connecting line of the centers of the mounting holes and the two end faces of the specimen along the length direction of the specimen.

The present invention has the following beneficial effects:

1). When the device works, the second fixture mechanism clamps and fixes the specimen, then the first fixture mechanism is connected to the second fixture mechanism and a common tension-compression or tension-compression+torsion fatigue testing machine, and then the fatigue crack measurement instrument is connected to the specimen. The testing machine drives the first and second fixture mechanisms to exert stretch, shear and torsion actions on the specimen, thus, the requirements of those tests on mode I, mode II, mode III and mixed-mode fatigue crack growth rates can be fully satisfied, and a good foundation is laid for precisely predicting the fatigue life of critical mechanical parts and engineering components under complex working conditions.

2). The long rod and the U-shaped clamping portion of each first fixture in the present invention are integrally formed and overcome the shortcoming of conventional split-type threaded fixtures, which are unable to effectively transfer fatigue torque. Meanwhile, the U-shaped clamping portion of the first fixture is connected to the loading hole on the flange plate in a fixed manner through fastening by a bolt and a nut. Under the precondition of assuring no lateral slide occurs during test, it makes the transfer of stretch-torsion fatigue load more stable and smoother.

3). The second fixture mechanism in the present invention comprises a first flange type fixture and a second flange type fixture. The first flange type fixture and the second flange type fixture clamp and fix a specimen from the two sides of the specimen respectively. Meanwhile, the mounting holes of the specimen are disposed symmetrically on the two sides of the machining notch. When clamping and fixing the specimen, the second fixture mechanism of the present invention sets aside the entire test portion of the specimen, thereby making for the testing of crack length and the observation of growth path during fatigue test.

4). In the test process, the specimen in the present invention can not only separately realize stretch, shear and torsion tests but also simultaneously realize two or three of the stretch, shear and torsion tests. In other words, the specimen in the present invention may satisfy mode I, mode II, mode III and mixed-mode fatigue crack growth tests in the same time. Therefore, the specimen in the present invention is also called a CTST (compact tension, shear and torsion) specimen. In addition to maintaining the advantage (large effective fatigue growth length) of a compact tension (CT) specimen, the CTST specimen in the present invention also can easily prefabricate a mode I fatigue crack.

5). The device provided by the present invention clamps and fixes a specimen between the first flange type fixture and the second flange type fixture through insulating bolts. The setting of the insulating bolts and insulating spacers blocks the current conduction between the two flange type fixtures and CTST specimen, and lowers the SNR (signal to noise ratio) of monitoring voltage signals during the fatigue test.

DESCRIPTION OF REFERENCE SIGNS 10-first fixture 11-long rod 12-U-shaped clamping portion 20A-first flange type fixture 20B-second flange type fixture 21-flange plate 22-flange neck 23-loading hole 24-clamp face 30-specimen 31-machining notch 32-mounting hole 33-closed end 40-fatigue crack measurement instrument 41-voltage probe 42-current probe 50-insulating bolt 60-fastening bolt 61-nut Detailed Description of the Embodiments Below the working process of the present utility model is further described by referring to accompanying drawings.

Figure 2:
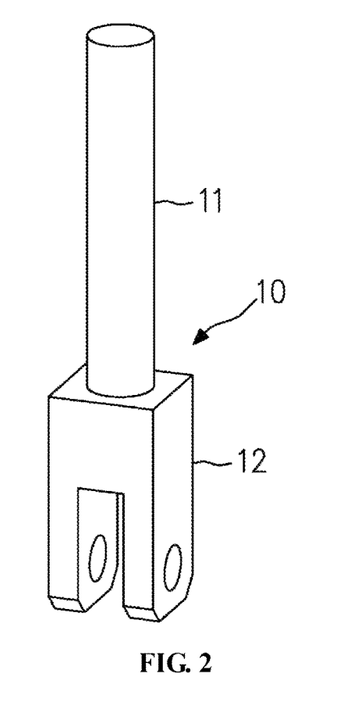
FIG. 2 is a structural schematic of a first fixture.
Figure 3:
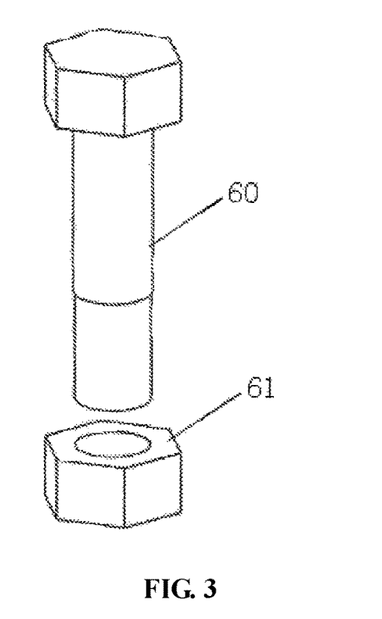
FIG. 3 is a structural schematic of a bolt and a nut connecting the U-shaped clamping portion of a first fixture and a loading hole on a flange plate.

As shown in FIG. 1~FIG. 10, this device for testing mixed-mode fatigue crack growth rate comprises the following components:

Two first fixtures 10, wherein one end of each first fixture 10 is designed as a cylindrical long rod 11 and the other end is designed as a U-shaped clamping portion 12 making for connection to the fixture in a second fixture mechanism; the long rod 11 and the U-shaped clamping portion 12 are integrally formed. As shown in FIG. 2, the U-shaped clamping portion 12 comprises two ear plates adjacent to and in parallel with each other, a clearance is disposed between two ear plates to make for accommodation of a flange plate 21, and process holes for the passage of a fastening bolt 60 are disposed on the two ear plates in a corresponding manner.

Figure 4:
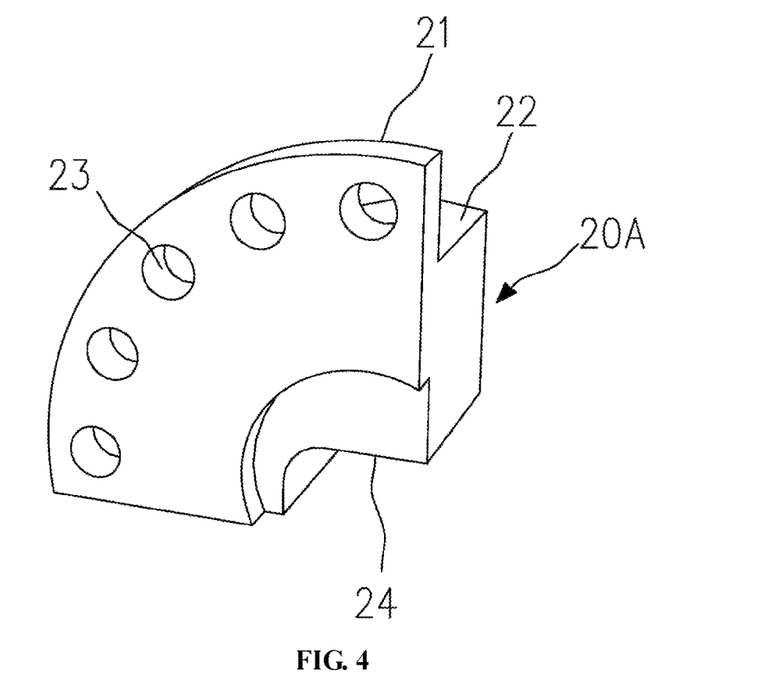
FIG. 4 is a structural schematic of a first flange type fixture.
Figure 5:
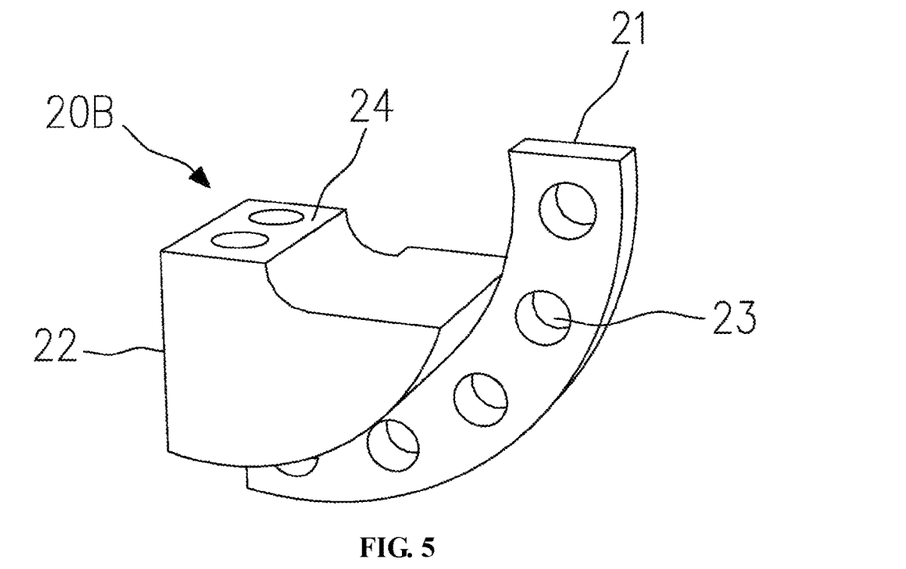
FIG. 5 is a structural schematic of a second flange type fixture.
Figure 6:
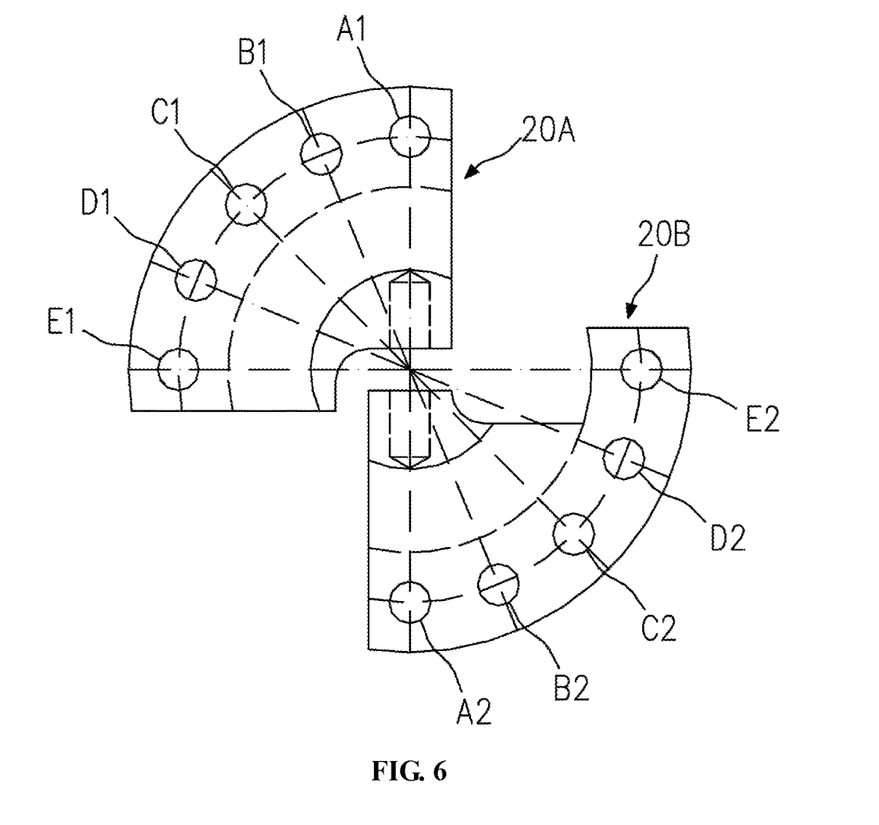
FIG. 6 and FIG. 7 are structural schematics for cooperation between a first flange type fixture and a second flange type fixture.

A first flange type fixture 20A and a second flange type fixture 20B, wherein each of the first flange type fixture 20A and the second flange type fixture 20B comprises integrally formed flange plate 21 and a flange neck 22; the flange plates 21 and the flange necks 22 are all sectorial, and a number of loading holes 23 penetrating the plate body are evenly distributed along the circumference of each flange plate 21 and on the arc edge of the flange plate 21 sticking out from the corresponding flange neck 22, as shown in FIG. 4, FIG. 5 and FIG. 6.

Figure 7:
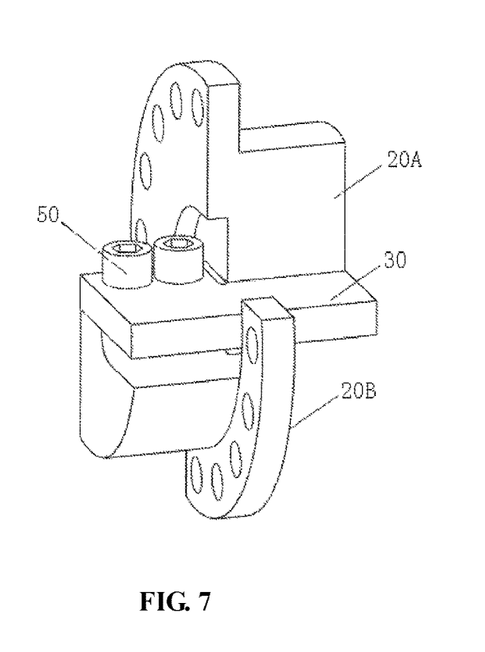

A clamp face 24 making for installation of the specimen 30 is disposed at the circle center of the sectorial flange neck 22 and perpendicular to the plane of the flange plate 21, and threaded holes are disposed on the clamp face 24. The flange neck 22 of the first flange type fixture 20A and the flange neck 22 of the second flange type fixture 20B clamp and fix the specimen 30 from the two side faces of the specimen 30 respectively. Insulating bolts 50 pass through the specimen 30 and stretch into the threaded holes on the clamp faces 24 to fasten the specimen 30 between two clamp faces 24. As shown in FIG. 7, insulating spacers are disposed between the clamp face 24 and the side face of the specimen 30. The flange plate 21 of the first flange type fixture 20A and the flange plate 21 of the second flange type fixture 20B in a clamping state are coplanar and have a same radius and circle center, as shown in FIG. 6. For the sake of conciseness, the specimen 30 is not shown in FIG. 6.

The flange plate 21 of the first flange type fixture 20A and the flange plate 21 of the second flange type fixture 20B are coplanar, that is, the planes of the two flange plates 21 on a same side coincide with each other or are on a same plane.

As shown in FIG. 6, the concentric angle corresponding to the flange plate 21 of the first flange type fixture 20A and the concentric angle corresponding to the flange plate 21 of the second flange type fixture 20B are both 90°, and five loading holes 23 are evenly distributed on each flange plate 21.

As shown in FIG. 6, loading hole A1 and loading hole A2 correspond to each other and their connecting line, i.e.: loading line, passes the circle center; loading hole B1 and loading hole B2 correspond to each other and their connecting line, i.e.: loading line, passes the circle center; loading hole C1 and loading hole C2 correspond to each other and their connecting line, i.e.: loading line, passes the circle center; loading hole D1 and loading hole D2 correspond to each other and their connecting line, i.e.: loading line, passes the circle center; loading hole E1 and loading hole E2 correspond to each other and their connecting line, i.e.: loading line, passes the circle center.

Figure 8:
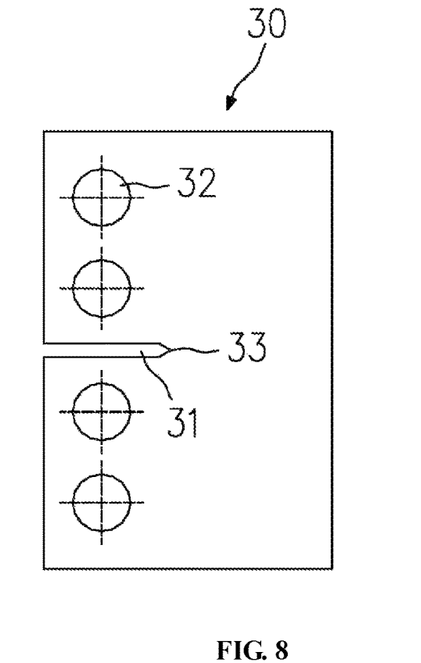
FIG. 8 is a structural schematic of a specimen.

As shown in FIG. 8, the plate-like specimen 30 is rectangular. A machining notch 31 stretching from the edge of the specimen 30 to the inside of the specimen 30 along the width direction of the specimen 30 is disposed on the specimen 30. The machining notch 31 is disposed in the middle of a long side of the specimen 30. The closed end 33 of the machining notch 31 inside the specimen 30 is in a peak shape. The crest line of the peak-shaped closed end 33 of the machining notch 31 is coplanar with the plane of prefabricated fatigue crack. Mounting holes 32 for the passage of the insulating connecting components are disposed on the two sides of the machining notch 31. The connecting line of the centers of the mounting holes 32 is perpendicular to the plane of the prefabricated fatigue crack.

Figure 9:
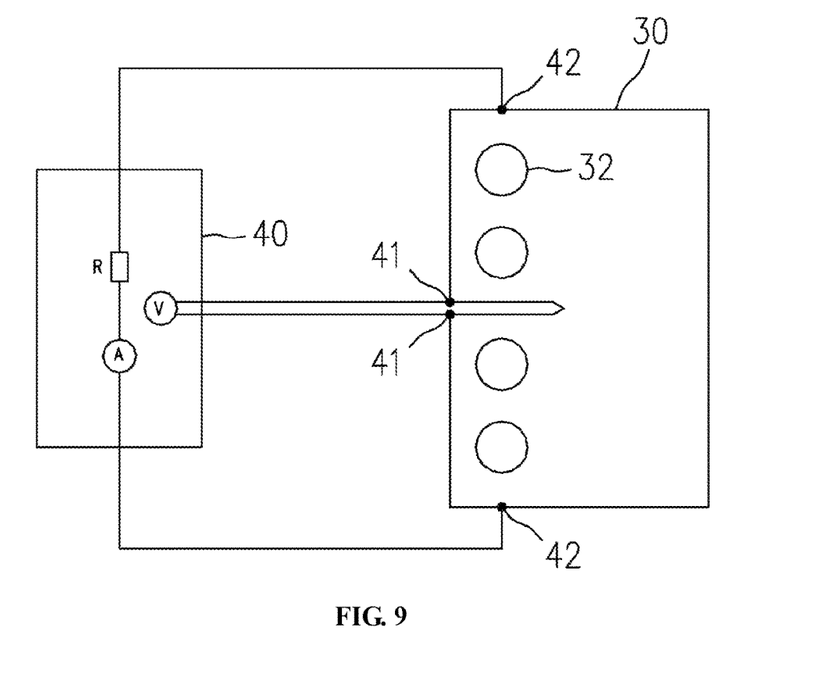
FIG. 9 is a structural schematic for connection between a DC potential fatigue crack measurement instrument and a specimen.

As shown in FIG. 9, the fatigue crack measurement instrument 40 is a DC potential fatigue crack measurement instrument. The two voltage probes 41 of the DC potential fatigue crack measurement instrument are connected to the two sides of the open end of the machining notch 31 respectively. The two current probes 42 of the DC potential fatigue crack measurement instrument are respectively connected to the intersections between the connecting line of the centers of the mounting holes 32 and the two end faces of the specimen 30 along the length direction of the specimen.

Figure 10:
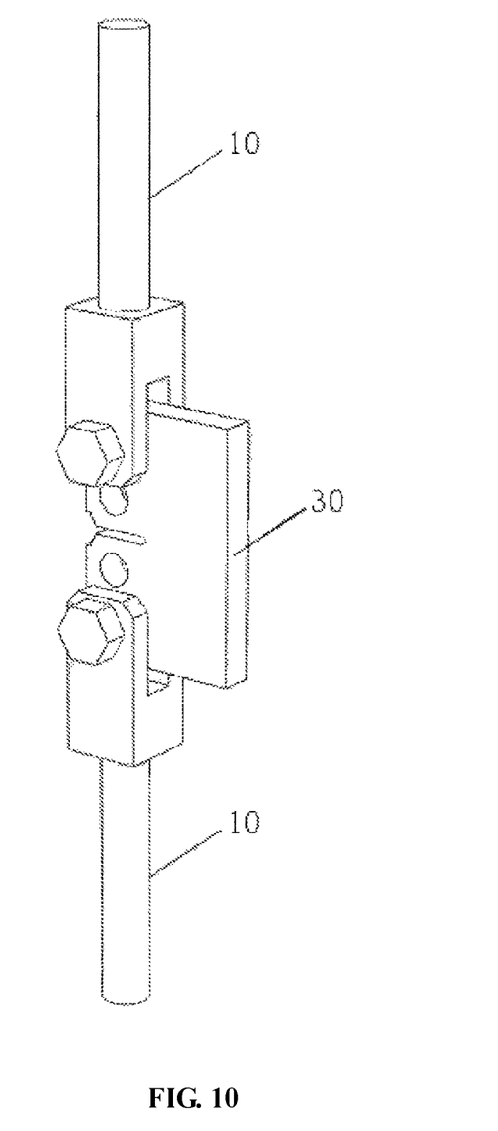
FIG. 10 is a structural schematic for prefabrication of a mode I fatigue crack on a specimen by a first fixture.

Below the test process of the present invention is described in details by referring to FIG. 1 and FIG. 10.

Figure 1:
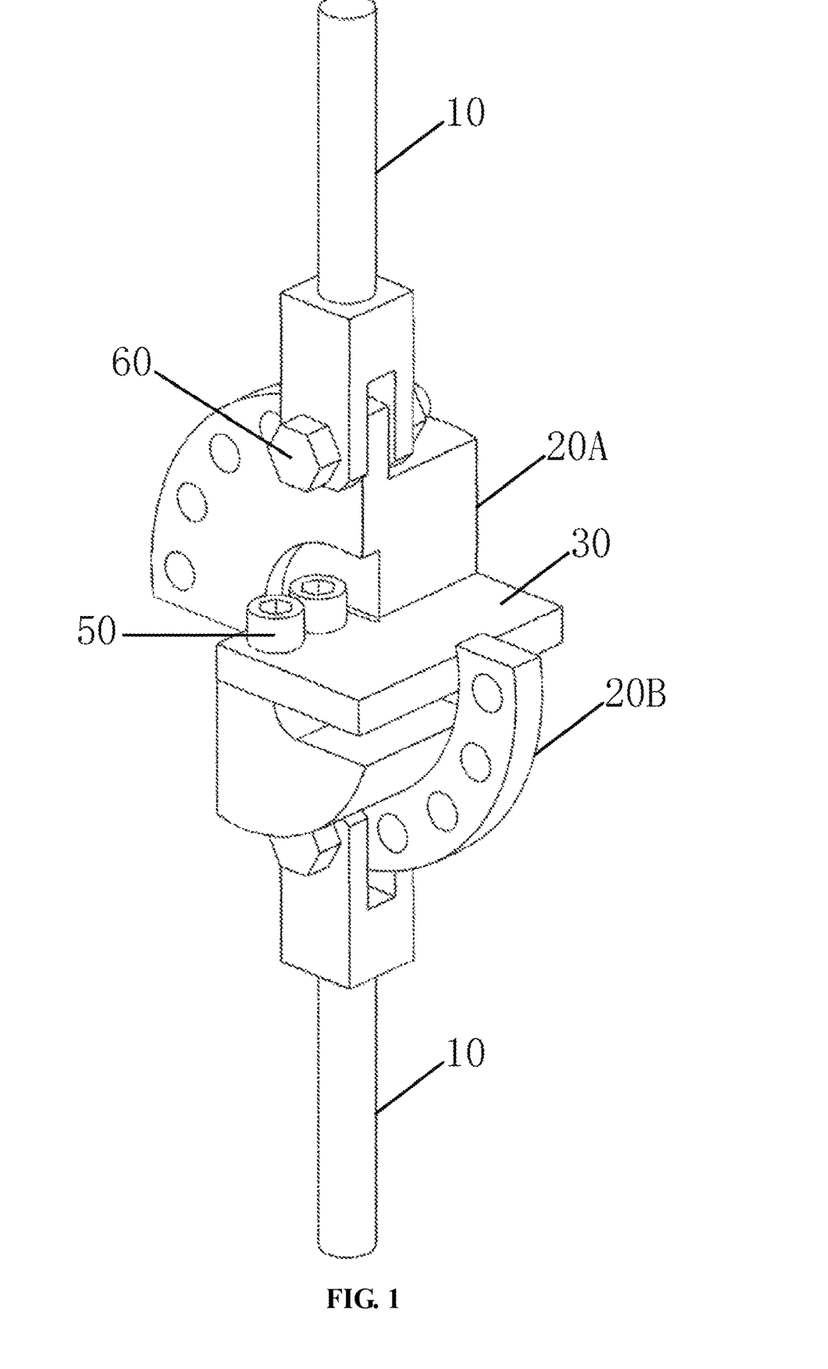
FIG. 1 is a structural schematic of the present invention.

The structure during test is as shown in FIG. 1. With the specimen 30 as the center, firstly the specimen 30 is connected to the clamp face 24 between the first flange type fixture 20A and the second flange type fixture 20B through four insulating bolts 50 in a fixed manner; then the screw of a fastening bolt 60 passes through the process hole on the ear plate of the U-shaped clamping portion 12 and the loading hole A1 on the flange plate 21 of the first flange type fixture 20A in turn and a nut 61 is screwed up on the extension end of the screw to make the first fixture 10 and the flange plate 21 of the first flange type fixture 20A connected in a fixed manner; then the screw of another fastening bolt 60 passes through the process hole on the ear plate of the U-shaped clamping portion 12 and the loading hole A2 on the flange plate 21 of the second flange type fixture 20B in turn and a nut 61 is screwed up on the extension end of the screw to make the first fixture 10 and the flange plate 21 of the second flange type fixture 20B connected in a fixed manner; then the two first fixtures 10 are connected to the fatigue testing machine, and lastly a DC potential crack measurement instrument 40 and the CTST specimen 30 are connected, the voltage probes 41, i.e.: conductors at the voltage test end are respectively connected near the open end of the machining notch 31, and the current probes 42, i.e.: current supply conductors are respectively connected to the intersections between the connecting lines of four mounting holes 32 of the specimen and the two end faces of the specimen 30 along the length direction of the specimen.

The loading line formed by linking the loading hole A1 and loading hole A2 is coplanar with the plane of the prefabricated fatigue crack generated on the specimen 30 when the two first fixtures 10 exert a stretch action, i.e.: a separate axial stretch load on the specimen 30.

When loading holes are changed to exert a new action on the specimen 30, the loading line obtained from the connecting line of the two changed loading holes still need to pass through the circle center of the two flange plates 21, and meanwhile the loading line obtained from the connecting line of the two changed loading holes is coplanar with the plane of the prefabricated fatigue crack generated on the specimen 30 when the two first fixtures 10 exert a stretch action, i.e.: a separate axial stretch load on the specimen 30.

The test method has the following steps:

1. As shown in FIG. 10, directly through fastening bolts 60 and nuts 61, two first fixtures 10, i.e.: integrated U-shaped fixtures, are connected to the two mounting holes 32 symmetrically distributed on the two sides of the machining notch 31 of the specimen 30, i.e.: CTST specimen.

The fatigue testing machine prefabricates a fatigue crack and obtains a plane of a prefabricated fatigue crack by exerting an axial stretch load on the specimen 30 through the first fixtures 10. In order to reduce the time the prefabrication of a fatigue crack takes, a higher load is adopted to generate a fatigue crack at first and then the load is shed level by level. The shedding rate at each level is not greater than 20%. The maximum force value at the last level of the prefabrication of a fatigue crack may not exceed the maximum force value at the time when recording of test data is started.

2. After a fatigue crack is prefabricated, the CTST specimen is removed from the first fixtures 10, i.e.: integrated U-shaped fixtures, and the CTST specimen is connected to the clamp face 24 between the first flange type fixture 20A and the second flange type fixture 20B via the insulating bolts 50. Insulating spacers are disposed between the clamp face 24 and the CTST specimen. Then the loading hole on the flange plate 21 of the first flange type fixture 20A and the loading hole on the flange plate 21 of the second flange type fixture 20B are connected to the U-shaped clamping portions of the two first fixtures 10, i.e.: integrated U-shaped fixtures. Then the DC potential crack measurement instrument 40 and the CTST specimen are connected according to the structure shown in FIG. 9, corresponding test frequency, waveform and load type and ratio are set, the needed mixed-mode fatigue crack growth test is done, mode II and mode III loading is realized through axial stretch via different holes, and mode I loading is realized through axial torsion.

3. Before start of a mixed-mode fatigue crack growth test, the DC potential crack measurement instrument is switched on to record the potential of the CTST specimen at every fatigue cycle. The test is paused once a specific number of cycles. Cellulose acetate membrane and acetone are adopted for surface replication (the cycle is subject to crack growth rate. In a section near the threshold value, replication may be measured at a cycle of $10^4 \sim 10^5$. In a Paris section, replication may be measured at a cycle of $10^3 \sim 10^4$. In a high-speed growth section, a higher frequency of replication is needed). Calibration test is done.

4. After the test is completed, the result of the calibration test is compared with the data recorded by the DC potential crack measurement instrument. The relation between crack length and measurement voltage is analyzed at different fatigue cycles and expressed with the following relational expression:

$$a/a_0 = P_0 + P_1(V/V_0) + P_2(V/V_0)^2 + P_3(V/V_0)^3 \quad (1)$$

Where, $a_0$, $a$, $V_0$ and $V$ are initial crack length, crack length, initial voltage value and measured voltage value respectively; $P_1$, $P_2$, $P_3$ and $P_4$ are fit coefficients. Through regression, a crack length-fatigue cycle curve is calculated, and then a fatigue crack growth rate is obtained through differential calculus, then the range of mixed mode stress intensity factor is obtained through calculation in combination with the value of finite element, and lastly a mixed-mode fatigue crack growth rate curve is obtained.

What is claimed is:

1. A device for testing mixed-mode fatigue crack growth rate, comprising a plate-like specimen, wherein the device comprises the following components:

a first fixture mechanism, for exerting stretch, shear and torsion actions on the specimen via a second fixture mechanism;

a second fixture mechanism, for clamping the specimen and enabling the specimen to generate a mixed-mode fatigue crack in cooperation with the first fixture mechanism; and a fatigue crack measurement instrument, for measuring and recording the length of mixed-mode fatigue crack generated on the specimen, wherein the first fixture mechanism comprises two first fixtures, one end of each first fixture is designed as a cylindrical long rod, and the other end is designed as a U-shaped clamping portion making for connection to the fixture in a second fixture mechanism; the long rod and U-shaped clamping portion are integrally formed.

2. The device for testing mixed-mode fatigue crack growth rate according to claim 1, wherein the second fixture mechanism comprises a first flange type fixture and a second flange type fixture both comprising integrally formed flange plate and flange neck;

the flange plates and the flange necks are all sectorial, and a number of loading holes penetrating the plate body are evenly distributed along the circumference of each flange plate and on the arc edge of the flange plate sticking out from the corresponding flange neck;

a clamp face making for installation of the specimen is disposed at the circle center of the sectorial flange neck and perpendicular to the plane of the flange plate, the flange neck of the first flange type fixture and the flange neck of the second flange type fixture clamp and fix the specimen from the two side faces of the specimen respectively and insulating connecting components pass through the specimen, stretch into the flange neck and fasten the specimen to the clamp face; insulating spacers are disposed between the clamp face and the side face of the specimen; the flange plate of the first flange type fixture and the flange plate of the second flange type fixture in a clamping state are coplanar and have a same radius and circle center;

the U-shaped clamping portion of the first fixture is connected to a loading hole on a flange plate via a connecting component in a fixed manner, the U-shaped clamping portions on the two first fixtures are connected to the flange plate of the first flange type fixture and the flange plate of the second flange type fixture respectively; the center of the loading hole on the flange plate of the first flange type fixture connected to a U-shaped clamping portion and the center of the loading hole on the flange plate of the second flange type fixture jointly constitute a loading line, the loading line passes through the circle center of the flange plates;

the loading line is coplanar with the plane of the prefabricated fatigue crack generated on the specimen when the two first fixtures exert a stretch action on the specimen.

3. The device for testing mixed-mode fatigue crack growth rate according to claim 2, wherein the plate-like specimen is rectangular, a machining notch stretching from the edge of the specimen to the inside of the specimen along the width direction of the specimen is disposed on the specimen, the machining notch is disposed in the middle of a long side of the specimen, and the closed end of the machining notch inside the specimen is in a peak shape, the crest line of the peak-shaped closed end of the machining notch is coplanar with the plane of the prefabricated fatigue crack, mounting holes for the passage of the insulating connecting components are disposed on the two sides of the machining notch, the connecting line of the centers of the mounting holes is perpendicular to the plane of the prefabricated fatigue crack.

4. The device for testing mixed-mode fatigue crack growth rate according to claim 2, wherein the concentric angle corresponding to the flange plate of the first flange type fixture and the concentric angle corresponding to the flange plate of the second flange type fixture are both 90°.

5. The device for testing mixed-mode fatigue crack growth rate according to claim 2, wherein 5~9 loading holes are evenly distributed on each flange plate, and the two flange plates have a same number of loading holes.

6. The device for testing mixed-mode fatigue crack growth rate according to claim 2, wherein the connecting components are fastening bolts, the screws of the bolts pass through the U-shaped clamping portions and the loading holes and connect the first fixtures and the flange plates, and the ends of the screws of the bolts sticking out from the U-shaped clamping portions are fastened with nuts.

7. The device for testing mixed-mode fatigue crack growth rate according to claim 3, wherein the insulating connecting components are insulating bolts, and threaded holes corresponding to the insulating bolts are disposed on clamp faces of the flange necks.

8. The device for testing mixed-mode fatigue crack growth rate according to claim 3, wherein the fatigue crack measurement instrument is a DC potential fatigue crack measurement instrument, the two voltage probes of the DC potential fatigue crack measurement instrument are connected to the two sides of the open end of the machining notch respectively, the two current probes of the DC potential fatigue crack measurement instrument are respectively connected to the intersections between the connecting line of the centers of the mounting holes and the two end faces of the specimen along the length direction of the specimen.

* * * * *